(12) United States Patent
Carder et al.

(10) Patent No.: US 10,550,959 B2
(45) Date of Patent: Feb. 4, 2020

(54) CONTROL VALVE MONITORING SYSTEM

(71) Applicant: FISHER CONTROLS INTERNATIONAL LLC, Marshalltown, IA (US)

(72) Inventors: Kenneth Harold Carder, Marshalltown, IA (US); Shawn W. Anderson, Haverhill, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 0 days.

(21) Appl. No.: 16/249,556

(22) Filed: Jan. 16, 2019

(65) Prior Publication Data

US 2019/0145544 A1    May 16, 2019

Related U.S. Application Data

(62) Division of application No. 15/293,016, filed on Oct. 13, 2016, now Pat. No. 10,197,185, which is a
(Continued)

(51) Int. Cl.
*F16K 37/00* (2006.01)
*G01H 1/00* (2006.01)
(Continued)

(52) U.S. Cl.
CPC ...... *F16K 37/0041* (2013.01); *F16K 37/0083* (2013.01); *G01H 1/00* (2013.01);
(Continued)

(58) Field of Classification Search
CPC ...... G01N 29/09; G01N 29/14; G01N 29/245; G01N 29/04; G01N 29/323;
(Continued)

(56) References Cited

U.S. PATENT DOCUMENTS 5,329,465 A    7/1994  Arcella et al.
5,433,245 A    7/1995  Prather et al.
(Continued)

FOREIGN PATENT DOCUMENTS

CA    2129470 A1    2/1995
CN    202230056 U    5/2012
(Continued)

OTHER PUBLICATIONS

Office Action for Canadian Patent Application No. 2840238 dated Apr. 29, 2019.
(Continued)

*Primary Examiner* — Suman K Nath
(74) *Attorney, Agent, or Firm* — Marshall, Gerstein & Borun LLP

(57) ABSTRACT

A control valve monitoring system is disclosed. The control valve monitoring system includes at least one sensor connected to one of a valve stem or valve shaft, and the at least one sensor detects a change in mechanical integrity of one of the valve stem or valve shaft. A device for providing data regarding the change in mechanical integrity of one of the valve stem or valve shaft is provided, allowing maintenance of the valve shaft or valve stem to be conducted in an efficient manner.

5 Claims, 4 Drawing Sheets

Related U.S. Application Data division of application No. 13/552,379, filed on Jul. 18, 2012, now Pat. No. 9,494,560.

(60) Provisional application No. 61/510,252, filed on Jul. 21, 2011.

(51) Int. Cl.
*G01N 29/14* (2006.01)
*G01N 29/24* (2006.01)
*G01N 29/09* (2006.01)

(52) U.S. Cl.
CPC .............. *G01N 29/09* (2013.01); *G01N 29/14* (2013.01); *G01N 29/245* (2013.01); *G01N 2291/0258* (2013.01); *G01N 2291/2626* (2013.01)

(58) Field of Classification Search
CPC ....... G01N 29/2437; G01N 2291/0258; G01N 2291/2626; H01L 41/22; F16K 37/0041; F16K 37/0083; G01H 1/00
USPC .......... 73/587, 592, 1.48, 1.72, 35.11, 35.13, 73/61.56
See application file for complete search history.

(56) References Cited

U.S. PATENT DOCUMENTS

| | | | |
|---|---|---|---|
| 5,747,697 A | 5/1998 | Johnson et al. | |
| 6,240,789 B1 | 6/2001 | Morlan et al. | |
| 7,152,482 B2 | 12/2006 | Ueno et al. | |
| 7,318,350 B2 | 1/2008 | Boken | |
| 7,881,567 B2 | 2/2011 | Bosselmann et al. | |
| 9,494,560 B2 | 11/2016 | Carder et al. | |
| 2003/0019297 A1 | 1/2003 | Fiebelkorn et al. | |
| 2005/0257618 A1 | 11/2005 | Boken | |
| 2007/0017506 A1 | 1/2007 | Bell et al. | |
| 2008/0034882 A1 | 2/2008 | Ohta et al. | |
| 2008/0204707 A1* | 8/2008 | Hwang | G01B 11/18 356/35.5 |
| 2008/0276995 A1 | 11/2008 | Ray et al. | |
| 2009/0161243 A1 | 6/2009 | Sharma et al. | |
| 2009/0317928 A1* | 12/2009 | Smelser | G02B 6/02114 438/31 |
| 2010/0236319 A1 | 9/2010 | Penman | |
| 2011/0108469 A1 | 5/2011 | Yamamoto et al. | |

FOREIGN PATENT DOCUMENTS

| | | |
|---|---|---|
| DE | 199 47 129 A1 | 4/2001 |
| EP | 0 390 224 A3 | 3/1991 |
| EP | 0 315 391 B1 | 4/1994 |
| EP | 0 637 713 A1 | 2/1995 |
| JP | H01-153881 A | 6/1989 |
| JP | H04-93652 | 3/1992 |
| JP | 2868861 B2 | 3/1999 |
| JP | 2004-184274 A | 7/2004 |
| JP | 2007-010646 A | 1/2007 |
| JP | 2010-502967 A | 1/2010 |
| JP | 2010-054434 A | 3/2010 |
| JP | 2010-237035 A | 10/2010 |

OTHER PUBLICATIONS

Notice of Reason for Rejection corresponding to Korean Application No. 10-2019-7004984 dated Mar. 21, 2019.
English Translation of First Office Action for Chinese Patent Application No. 201110212566.7, dated Dec. 15, 2015.
English Translation of Office Action for Japanese Patent Application No. 2014-521706, dated Jun. 29, 2016.
English Translation of Office Action, Final Decision of Rejection for Japanese Patent Application No. 2014-521706, dated Mar. 1, 2017.
Examination Report for European Application No. 16160541.5 dated Mar. 8, 2017.
Examination Report for European Application No. 16160541.5 dated Oct. 12, 2017.
Examination Report for GCC Patent Application No. 2012-21792, dated Aug. 22, 2016.
Extended European Search Report for Application No. 16160541.5 dated Jun. 30, 2016.
GCC Patent Office, Examination Report for GCC Patent Application No. GC 2012-33915, dated May 14, 2018.
IMPI Office Action, Mexican Patent Application No. MX/a/2014/000841, dated Apr. 19, 2016.
IMPI Office Action, Mexican Patent Application No. MX/a/2016/011613, dated Jul. 18, 2017.
International Preliminary Report on Patentability for Application No. PCT/US2012/047039, dated Jan. 21, 2014.
International Search Report for PCT/US2012/047039, dated Sep. 11, 2012.
Korean Intellectual Property Office Notice of Reason for Rejection (Office Action) dated Jul. 30, 2018.
Office Action for Canadian Patent Application No. 2840238 dated Jul. 26, 2018.
Park et al. Overview of Piezoelectric Impedance-Based Health Monitoring and Path Forward Shock and Vibration Digest, © 2003 Sage Publications v.35, No. 6, pp. 451-463.
State Intellectual Property Office (SIPO), Second Office Action for Chinese Patent Application No. 201110212566.7, dated Aug. 10, 2016, SIPO, China.
State Intellectual Property Office (SIPO), Thrid Office Action for Chinese Patent Application No. 201110212566.7, dated Feb. 20, 2017, SIPO, China.
The Federal Institute of Industrial Property (FIIP), First Office Action for Russian Patent Application No. 201410371, dated May 24, 2016.
Wang et al., Impedance Analyisis and Damage Detection on Piezoelectric Smart Beam, Chinese Journal of Solid Mechanic, China Academic Journal Electronic Publishing House, © 1994-2015. Dec. 2008, pp. 402-407, vol. 29 No. 4, China.
Written Opinion for PCT/US2012/047039, dated Sep. 11, 2012.
Notice of Reason for Rejection corresponding to Korean Application No. 10-2019-7004984 dated Jul. 16, 2019.

* cited by examiner

CONTROL VALVE MONITORING SYSTEM

CROSS-REFERENCE TO RELATED APPLICATIONS

This application is a division of U.S. patent application Ser. No. 15/293,016, filed Oct. 13, 2016, which is a divisional of U.S. patent application Ser. No. 13/552,379, filed Jul. 18, 2012, which claims the benefit of U.S. Application No. 61/510,252, filed Jul. 21, 2011, all of which are hereby incorporated by reference in their entirety herein.

FIELD OF THE DISCLOSURE

The present disclosure relates generally to maintenance of control valves and, more specifically, to a system for detecting shaft and stem fatigue in a control valve.

BACKGROUND OF THE DISCLOSURE

A control valve regulates the rate of fluid flow as the position of a valve plug or disk is changed by force from an actuator. To do this, the control valve must: (1) contain the fluid without external leakage; (2) have adequate capacity for the intended service; (3) be capable of withstanding the erosive, corrosive, and temperature influences of the process; and (4) incorporate appropriate end connections to mate with adjacent pipelines and actuator attachment means to permit transmission of actuator thrust to the valve plug stem or rotary shaft, for example.

Many styles of control valves are known. For example, sliding-stem control valves and rotary-shaft control valves are well known in the field of process control valves. Sliding-stem control valves include globe valves, which are valves having a linear motion closure member, one or more ports, and a body distinguished by a globular shaped cavity around a port region. Sliding-stem control valves typically employ a plug for their closure member that is positioned in the flow path to modify the rate of flow through the valve. The sliding-stem control valve further includes a valve stem having a first end connected to the closure member and a second end opposite the first end that is connected to an actuator.

A rotary-shaft control valve is a valve in which the flow control member, such as a full ball, partial ball, sphere or disk, is rotated in the flowstream to control the capacity of the valve. The rotary-shaft control valve includes a shaft that corresponds to the valve stem of a globe or sliding-stem valve.

Some methods of detecting fatigue and an onset of cracking in a shaft of a rotary-shaft control valve or a stem of a sliding-stem control valve are known. For example, it is known to mount strain gauges on control valve stems and shafts to verify that a force or torque has been transmitted to the valve once a positioner and an actuator have been given a control signal to close.

It is desired, however, to detect cracks in the valve stem or shaft that are too small to be identified by visual inspection, for example. It is also desired to detect cracks and fatigue in the valve stem and shaft earlier and more accurately than current methods allow. By doing so, end users are alerted that the control valve is in need of replacement parts and service, promoting more efficient maintenance and a longer useful life of the control valve.

SUMMARY OF THE DISCLOSURE

A control valve monitoring system comprises at least one sensor connected to one of a valve stem or valve shaft and a device for providing data regarding the change in mechanical integrity of one of the valve stem or valve shaft. The at least one sensor of the control valve monitoring system may be one of an acoustic emission sensor or an active ultrasonic sensor. The acoustic emission sensor may detect cracking in one of the valve shaft or valve stem through a change in acoustic signature, and the acoustic emission sensor may be attached to an end of the valve shaft or valve stem. The at least one sensor may also be one of a piezoelectric wave active sensor or a piezoceramic (PZT) sensor, such that the impedance of one of the piezoelectric wave active sensor and the PZT sensor to the valve shaft or stem may be correlated to the impedance of the valve shaft or valve stem, allowing a change in mechanical integrity of the valve shaft or valve stem to be detected.

Further, the piezoelectric wave active sensor or the PZT sensor may be attached to an outer diameter of a valve shaft or valve stem between a valve control and an actuator. In addition, the at least one sensor may be an optical fiber Bragg grating (FBG) sensor. The FBG sensor may measure strain at a localized area of the valve shaft or valve stem. Further, the FBG sensor may be attached to an outer diameter of the valve shaft or valve stem between a valve control and an actuator. Still further, the at least one sensor may be wireless. The at least one sensor may be incorporated into the valve stem or valve shaft during manufacture of the valve stem or valve shaft. The at least one sensor may be attached to the valve shaft or valve stem by one or more of a bonding agent, a soldering agent, or a bolt. The control valve monitoring system may further include a memory and a power source for data gathering and reporting of faults in the valve shaft or valve stem.

In another example of the disclosure, a method of detecting a change in mechanical integrity of a valve shaft of a rotary-shaft control valve or a valve stem of a sliding-stem control valve comprises integrating at least one sensor into a valve shaft or a valve stem and sensing fatigue in the valve shaft or valve stem using structural health monitoring technology.

DETAILED DESCRIPTION OF THE DISCLOSURE

Figure 1:
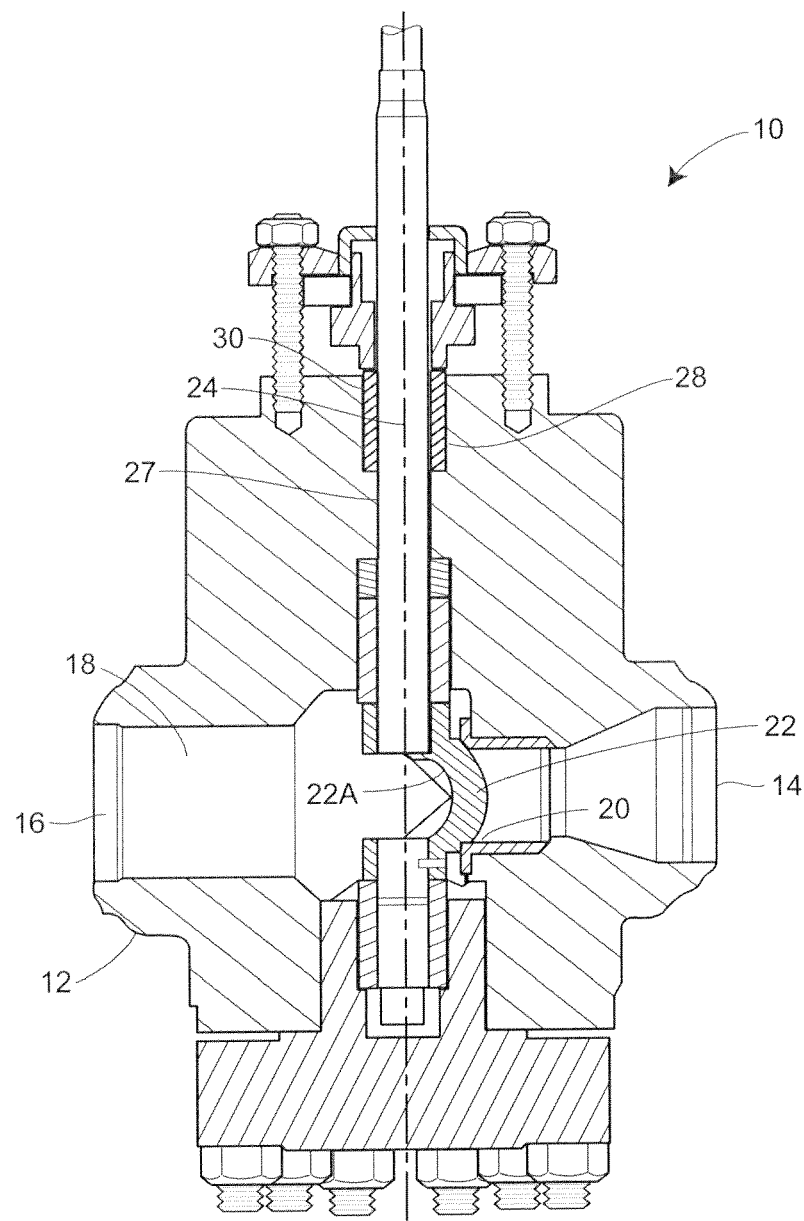
FIG. 1 is a cross-sectional view of a rotary-shaft control valve.

Referring now to FIG. 1, a rotary-shaft control valve 10 is illustrated. The rotary-shaft control valve 10 includes a valve body 12, a valve inlet 14, a valve outlet 16, and a flow passage 18 that extends between the valve inlet 14 and the valve outlet 16. The flow passage 18 includes a control passage 20, and a moveable control element 22 is moveably disposed in the control passage 20. The control element 22 is a rotary control element 22A that is connected to a valve shaft 24. The control element 22A may be, for example, a valve disk, a partial or full ball, or any other form of rotating } control element. The valve shaft 24 is operatively coupled to an actuator (not shown), which may be any kind of actuator commonly employed in the art.

The control element 22 is positioned such that the control element 22 is disposed within the control passage 20, and the position of the control element 22 within the passage 20 can be controlled using the actuator (not shown), controlling the amount of fluid flow through the control passage 20. The control valve 10 includes a bore 27 that is sized to receive the valve shaft 24. The valve body 12 includes a packing box 28, and a primary packing set 30 is disposed in the packing box 28. The packing set is sized to fit around the valve shaft 24.

Figure 2:
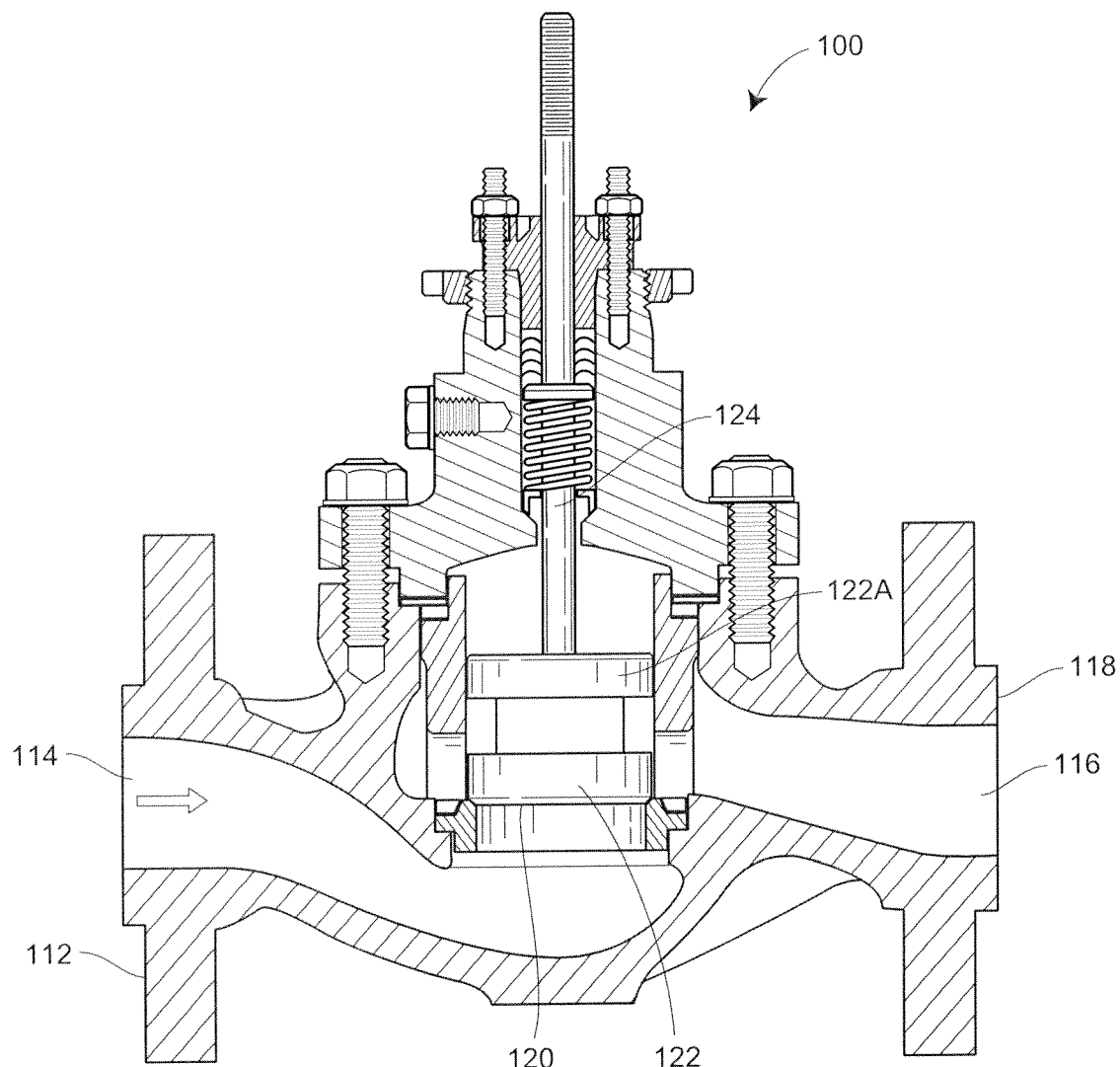
FIG. 2 is a cross-sectional view of a sliding-stem control valve.

Referring now to FIG. 2, a sliding-stem control valve 100 is illustrated Like the rotary-shaft control valve 10, the sliding-stem control valve 100 also includes a valve body 112, a valve inlet 114, a valve outlet 116, and a flow passage 118 extending between the valve inlet 114 and the valve outlet 116. The flow passage 118 also includes a control passage 120, and a moveable control element 122 disposed in the control passage 120. The control element 122 is a linear control element 122A, such as a plug, that is connected to a first end of a valve stem 124. A second end of the valve stem 124 disposed opposite the first end is operatively connected to an actuator (not shown) commonly employed in the art.

Figure 3:
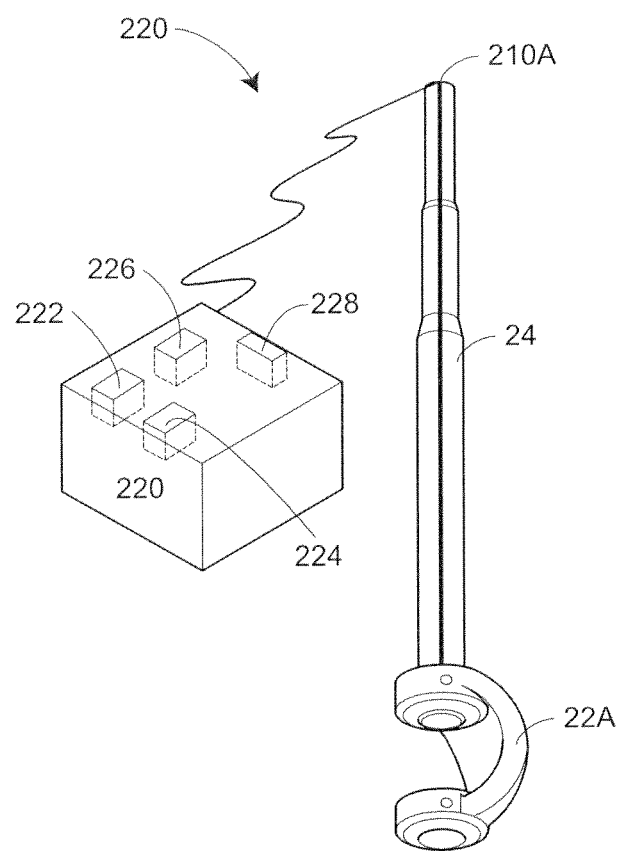
FIG. 3 is a perspective view of a shaft of the rotary-shaft control valve of FIG. 1 having a control valve monitoring system incorporated therein.

Referring now to FIG. 3, the shaft 24 of the rotary-shaft control valve 10 of FIG. 1 is illustrated. The shaft 24 includes a portion of the rotary control element 22A at one end. A control valve monitoring system 200 is integrated into the shaft 24. In a similar manner, the control valve monitoring system 200 may also be integrated into the stem 124 of the sliding-stem control valve 100 of FIG. 2. The control valve monitoring system 200 includes a sensor 210 for detecting an onset of cracking or change in material property of the shaft 24 or stem 124. More specifically, an acoustic emission sensor 210A is attached to one end of the valve shaft 24 or stem 124 via a bolt or other attachment mechanism. The acoustic emission sensor 210A detects a change in the mechanical integrity of the valve shaft 24 or stem 124 (FIG. 2) through a change in acoustic signature using structural health monitoring (SHM) technology.

Generally, SHM is the process of implementing a damage detection and characterization strategy for engineering structures. Damage is often defined as changes to the material and/or geometric properties of a structural system, which adversely affect the system's performance. The SHM process involves observing a system over time using periodically sampled dynamic response measurements from an array of sensors, the extraction of damage-sensitive features from these measurements, and the statistical analysis of these features to determine the current state of the system health. See, e.g., http://en.wikipedia.org/wiki/Structural_health_monitoring, Apr. 13, 2011.

The control valve monitoring system 200 further includes a device 220 for providing data regarding the change in mechanical integrity of one of the valve stem 124 or valve shaft 24. The device 220 may be a local digital valve positioner, a stand alone device for data collection/reduction, an asset management software package, or a control system, such as a Delta V control system.

Referring back now to FIG. 3, the sensor 210A detects a change in the mechanical integrity of the valve shaft 24 or stem 124 (FIG. 2) through a change in acoustic signature between the sensor 210A and the valve shaft 24 or stem 124. Data regarding the change in the mechanical integrity of the valve shaft 24 or stem 124 (FIG. 2) is then provided to an end user. More specifically, a detected fault or deviation from a baseline signature may be communicated to a local digital valve positioner, a stand alone device for data collection/reduction, an asset management software package, or a control system, such as Delta V, each of which may be a part of the control valve monitoring system 200. In one example, the detected fault triggers an alert in the digital valve positioner or data collection system (not shown), which would provide an indication of change in state or impending failure of the valve shaft 24 or stem 124. If the sensor 210A indicates shaft 24 or stem 124 (FIG. 2) crack detection, the end user is allowed time to prepare for maintenance of the valve shaft 24 or stem 124. In another example, the system 200 may also determine a rate of change of the detected damage and could, therefore, provide an estimate of remaining useful life of the component.

Figure 4:
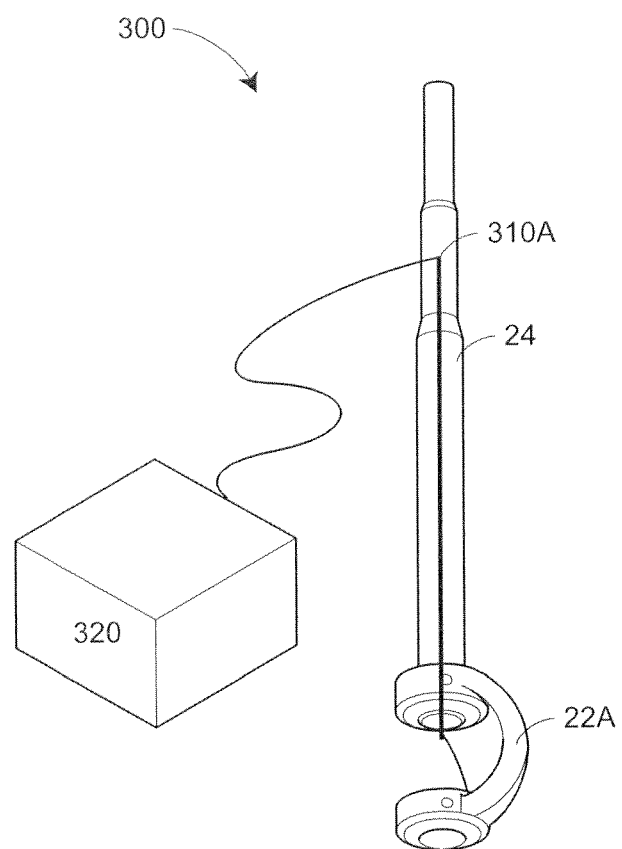
FIG. 4 is a perspective view of a shaft of the rotary-shaft control valve of FIG. 1 having another embodiment of a control valve monitoring system incorporated therein.

Referring now to FIG. 4, the shaft 24 of the rotary-shaft control valve 10 of FIG. 1 is again illustrated with another control valve monitoring system 300 using SHM technology. In a similar manner, the control valve monitoring system 300 may also be used with the stem 124 of the sliding-stem control valve 100 of FIG. 2. The control valve monitoring system 300 includes at least one sensor 310A that may be an optical fiber Bragg grating (FBG) sensor 310A for detecting a crack or change in material property of the shaft 24 or stem 124. The FBG sensor 310A is attached via bonding or soldering to an outer diameter of the shaft 24 or stem 124 between the valve element 22A and the actuator (not shown) disposed on an end of the shaft 24 opposite the valve element 22A. The FBG sensor 310A measures strain at a localized area on the shaft 24 or stem 124 (FIG. 2). By doing so, the control valve monitoring system 300 incorporates physical characteristic measurements of the valve shaft 24 or stem 124 (instead of an inferred or calculated estimation of component fatigue), providing time for an end user to prepare for maintenance of the valve shaft 24 or stem 124.

The sensor 310A of the control valve monitoring system 300 may alternatively be an active ultrasonic sensor that detects a change in the mechanical integrity of the valve shaft 24 or stem 124 (FIG. 2) through the change in ultrasonic Lamb waves between the ultrasonic sensor and the valve shaft 24 or stem 124. More specifically, the active ultrasonic sensor and actuator give the valve shaft 24 or stem 124 (FIG. 2) material a little pinch and then wait to record the resultant ultrasonic waves that propagate through the component. Cracks or other defects in the valve shaft 24 or stem 124 material will distort the reflected waves. These active ultrasonic sensors may be attached via bonding or soldering to an outer diameter of the shaft 24 or stem 124 or the end of the shaft 24 or stem 124, as illustrated for example in FIG. 3. However, the active ultrasonic sensors tend to be mounted on the end of the valve shaft 24 for rotary valves and the outer diameter of the valve stem 124 (FIG. 2) for sliding stem valves (FIG. 2).

In yet another embodiment, the sensor 310A of the control valve monitoring system 300 may be one or more of a piezoelectric wave active sensor or a piezoceramic (PZT) sensor. In this case, the impedance of the piezoelectric wave active sensor or the PZT sensor (FIG. 2) is correlated to the impedance of the shaft 24 or stem 124, allowing a change in mechanical integrity of the valve shaft 24 or stem 124 to be detected.

Like the control valve monitoring system 200 of FIG. 3, the control valve monitoring system 300 further includes a device 320 for providing data regarding the change in mechanical integrity of one of the valve stem 124 or valve shaft 24. The device 220 may be a local digital valve positioner, a stand alone device for data collection/reduction, an asset management software package, or a control system, such as a Delta V control system.

While the sensors 210A and 310A may be attached to the valve shaft 24 and stem 124 using a bonding agent, a soldering agent, bolts or other attachment mechanisms known to those of skill in the art, the sensors 210A and 310A may alternatively be incorporated into the valve shaft 24 or stem 124 during manufacture of the same.

Still further, for acoustic or ultrasonic measurements, the sensors 210A and 310A may be connected to the local digital valve positioner or stand alone device for data collection/reduction using a single cable or wireless signal (not shown). For the Fiber Bragg Grating (FBG) design, the sensors 210A and 310A may be connected to the digital valve positioner or stand alone device using optical fiber. When using multiple FBG sensors on one control valve assembly, many FBG sensors may be connected in series using a single optical fiber. For acoustic or ultrasonic measurements, each sensor 210A, 310A may be on its own cable or wireless address. Using wireless sensors with the control valve monitoring systems 200, 300 helps ease installation costs of the sensors 210A and 310A and eliminates fatigue of cable assemblies associated with the sensors 210A and 310A physically attached to the valve shaft 24 and stem 124 by various attachment mechanisms noted above.

In addition, the control valve monitoring systems 200, 300 may also include power and memory devices that allow for constant data gathering and reporting of faults.

Numerous modifications and alternative embodiments of the disclosure will be apparent to those skilled in the art in view of the foregoing description. Accordingly, this description is to be construed as illustrative only and is for the purpose of teaching those skilled in the art the best mode of carrying out the invention. The details of the present disclosure may be varied without departing from the spirit of the invention, and the exclusive use of all modifications that are within the scope of the claims is reserved.

Thus, while particular embodiments and applications have been illustrated and described, it is to be understood that the disclosed embodiments are not limited to the precise construction and components described herein. For example, those skilled in the art will appreciate that the outer diameter of the shaft 24 or stem 124 to which at least one sensor 210A (FIG. 3), 310A (FIG. 4) is attached is equivalent to an outer surface of the shaft 24 or stem 124. In addition, while the two control valve monitoring systems 200, 300 described herein are illustrated in FIGS. 3 and 4 as being integrated into the shaft 24 of the rotary-shaft control valve 10 of FIG. 1, the two control valve monitoring systems 200, 300 can also be fully integrated into the stem 124 of the sliding-stem control valve 100 of FIG. 2. Still further, those skilled in the art will also appreciate that the devices 220, 320 for providing data regarding the change in mechanical integrity of one of the valve stem 124 or valve shaft 24 may include one or more of a processor, a memory, a battery, and a wireless interface and still fall within the spirit and scope of the appended claims. In one example, the device 220 of FIG. 3 includes a processor 222, a memory 224, a battery 226, and a wireless interface 228, and the device 320 of FIG. 4 may also include one or more of the same. In sum, and as explained herein, these various modifications and others may be made in the arrangement, operation and details of the system and method disclosed herein without departing from the scope defined in the appended claims.

What is claimed is:

1. A control valve monitoring system comprising:
    at least one sensor connected to one of a valve stem or valve shaft, the sensor for detecting a change in mechanical integrity of one of the valve stem or valve shaft, wherein the at least one sensor is an optical fiber Bragg Grating (FBG) sensor; wherein the optical fiber Bragg grating (FBG) sensor measures strain at a localized area of the valve shaft or valve stem;
    a device for providing data regarding the change in mechanical integrity of one of the valve stem or valve shaft, and
    wherein the FBG sensor is attached to an outer surface of the valve stem or the valve shaft between an end of the valve stem or the valve shaft connected to a control element and another end of the valve stem or the valve shaft opposite to the control element by one of a bonding agent or a soldering agent.

2. The control valve monitoring system of claim 1, wherein the at least one sensor is wireless.

3. The control valve monitoring system of claim 1, further including memory and a power source for constant data gathering and reporting of faults in the valve shaft or valve stem.

4. A method of detecting a change in mechanical integrity of a valve shaft of a rotary-shaft control valve or a valve stem of a sliding-stem control valve, the method comprising:
    integrating at least one sensor into a valve shaft or a valve stem, wherein the at least one sensor is an optical fiber Bragg Grating (FBG) sensor;
    measuring strain at a localized area of the valve shaft or valve stem using the optical fiber Bragg grating (FBG) sensor;
    sensing fatigue in the valve shaft or valve stem via the FBG sensor by measuring the strain,
    wherein integrating at least one sensor into the valve shaft or the valve stem comprises attaching, via one of the bonding agent or a soldering agent, the FBG sensor to an outer surface of the valve stem or the valve shaft between an end of the valve stem or the valve shaft connected to a control element and another end of the valve stem or the valve shaft opposite to the control element, allowing a change in mechanical integrity of one of the valve shaft or the valve stem to be detected.

5. The method of claim 4, further comprising providing data regarding the change in mechanical integrity of the valve shaft or valve stem to one or more of a local digital valve positioner, a standalone device for data collection and reduction, an asset management software package, or a control system.

* * * * *

UNITED STATES PATENT AND TRADEMARK OFFICE
CERTIFICATE OF CORRECTION

PATENT NO. : 10,550,959 B2  
APPLICATION NO. : 16/249556  
DATED : February 4, 2020  
INVENTOR(S) : Kenneth Harold Carder et al.

Page 1 of 1

It is certified that error appears in the above-identified patent and that said Letters Patent is hereby corrected as shown below:

In the Specification

At Column 1, Line 7, "2016," should be -- 2016, now U.S. Pat. No. 10,197,185, --.

At Column 1, Line 9, "2012," should be -- 2012, now U.S. Pat. No. 9,494,560, --.

At Column 3, Line 15, "illustrated" should be -- illustrated. --.

Signed and Sealed this  
Tenth Day of November, 2020

Andrei Iancu  
*Director of the United States Patent and Trademark Office*